(12) United States Patent
Nader et al.

(10) Patent No.: US 6,606,405 B1
(45) Date of Patent: Aug. 12, 2003

(54) WOOD CHIPS ANALYSER

(75) Inventors: Joseph Nader, Montreal (CA); Réal Frenette, Pointe-Claire (CA)

(73) Assignee: Autolog Inc., Quebec (CA)

( * ) Notice: Subject to any disclaimer, the term of this patent is extended or adjusted under 35 U.S.C. 154(b) by 0 days.

(21) Appl. No.: 09/492,427

(22) Filed: Jan. 27, 2000

(30) Foreign Application Priority Data

Jan. 27, 1999 (CA) .............................................. 2258982

(51) Int. Cl.$^7$ ................................................ G06K 9/00
(52) U.S. Cl. ...................................... 382/154; 209/587
(58) Field of Search ............................... 382/100, 154; 348/86, 89, 128; 356/402, 407, 425; 250/341.8, 910, 339.1, 223 R; 209/517, 518, 576, 577, 580, 581, 587, 938

(56) References Cited

U.S. PATENT DOCUMENTS 4,825,068 A * 4/1989 Suzuki et al. ........... 250/223 R
5,781,230 A * 7/1998 Nguyen et al. ............. 348/128
6,175,092 B1 * 1/2001 Binette et al. .............. 209/587

* cited by examiner

*Primary Examiner*—Samir Ahmed
*Assistant Examiner*—Vikkram Bali
(74) *Attorney, Agent, or Firm*—Sughrue Mion, PLLC

(57) ABSTRACT

The present invention concerns a wood chips analyser. A sample of a load of chips is weighed, and then inserted into the analyser. A sifting drum sifts out any dust present in the sample. The chips are then spread out through the use of a spreader drum and two vibrating trays, which insure that the chips are oriented horizontally. The chips are then fed to a transparent conveyor. A pair of cameras are arranged about the conveyor, one camera facing each surface of the conveyor. The output of the cameras is sent to a controller, which makes a three-dimensional representation of each chip. Once the sample have been analysed, a report is generated according to modifiable criteria. A typical report will indicate the percentage of a category of chips. This information is then used by paper mills to treat the chips accordingly.

5 Claims, 4 Drawing Sheets

Sample total weight (air-dried): 1150.0 g

Optical sorting (percent of measured volume)

| Length (in) | Thickness (mm) | | | | | | Total | Norm | Difference |
|---|---|---|---|---|---|---|---|---|---|
| | 0 - 2 | 2 - 4 | 4 - 6 | 6 - 8 | 8 - 10 | 10 - 12 | 12+ | | | |
| Dust and fines | 0.8 | 0.1 | 0.0 | 0.0 | 0.0 | 0.0 | 0.0 | 0.9 | max 1.5% | 0.6% |
| 3/16 - 3/8 | 2.2 | 7.8 | 8.2 | 0.2 | 0.0 | 0.0 | 0.0 | 18.4 | | 15.2% |
| 3/8 - 5/8 | 3.5 | 12.4 | 13.4 | 7.9 | 6.2 | 0.2 | 0.0 | 43.6 | min 80.0% | |
| 5/8 - 7/8 | 3.1 | 7.6 | 7.6 | 3.9 | 3.7 | 2.1 | 2.2 | 30.2 | | |
| 7/8 - 1 1/8 | 0.0 | 0.1 | 0.4 | 0.2 | 0.9 | 0.5 | 0.9 | 3.0 | max 15.0% | 11.1% |
| Oversized | 0.0 | 0.0 | 0.2 | 0.4 | 0.9 | 0.6 | 1.8 | 3.9 | | |
| Total | 9.6 | 28.0 | 29.8 | 12.6 | 11.7 | 3.4 | 4.9 | 100.0 | | |
| Norm | max 5.0% | | min 80.0% | | | max 15.0% | | | | |
| Difference | -4.6% | | -9.6 | | | -5.0% | | | | |

FIG. 2

Emulation of mechanical sorting (percent of measured volume)

| Length (in) | 0 - 2 | 2 - 4 | 4 - 6 | 6 - 8 | Thickness (mm) 8 - 10 | 10 - 12 | 12+ | Total | Norm | Difference |
|---|---|---|---|---|---|---|---|---|---|---|
| Dust and fines | 0.9 | 0.0 | 0.0 | 0.0 | 0.0 | 0.0 | 0.0 | 0.9 | max 1.5% | 0.6% |
| 3/16 - 3/8 | 2.5 | 7.9 | 8.4 | 0.0 | 0.0 | 0.0 | 0.0 | 18.8 | min 80.0% | 14.7% |
| 3/8 - 5/8 | 3.9 | 12.1 | 13.2 | 8.8 | 6.1 | 0.2 | 0.0 | 44.3 | | |
| 5/8 - 7/8 | 2.6 | 7.7 | 5.8 | 4.2 | 2.6 | 2.3 | 2.9 | 28.1 | | |
| 7/8 - 1 1/8 | 0.0 | 0.1 | 0.4 | 0.3 | 0.9 | 0.7 | 1.1 | 3.5 | max 15.0% | 10.6% |
| Oversized | 0.0 | 0.0 | 0.2 | 0.5 | 0.8 | 0.9 | 2.0 | 4.4 | | |
| Total | 9.9 | 27.8 | 28.0 | 13.8 | 10.4 | 4.1 | 6.0 | 100.0 | | |
| Norm | max 5.0% | min 80.0% | | | | max 15.0% | | | | |
| Difference | -4.9% | -10.4 | | | | -5.5% | | | | |

| Dust | Weight: 0.0 g | Percentage: 0.0% | Norm: max 0.8% | Difference: 0.8% |
|---|---|---|---|---|

FIG. 3

WOOD CHIPS ANALYSER

FIELD OF THE INVENTION

The present invention relates to an analyser for wood chips. Such an apparatus is useful in the paper-making industry.

DESCRIPTION OF THE PRIOR ART

In very general terms, paper is made by mulching chips into a pulp, and then pressing this pulp to extract water and dry it so as to make paper.

The analysis of wood chips is extremely important for the paper industry. Paper mills require that the chips used for making paper have sizes within a predetermined range. If a percentage of the chips lies outside the range, the paper mill can require that the chips producer pay a fine, partly to offset the cost of chemicals necessary to "digest" the offending chips.

There are a few machines that exist to analyse the chips, generally based on the principle of sifting a sample of the load of chips in a number of mechanical sieves having progressively smaller holes or openings. Once the sample has been sieved, weight percentages are established according to the sizes of the sieves. These machines have the distinct disadvantage of not providing accurate results. Furthermore, when the chips are sifted, they can inadvertently be oriented vertically instead of horizontally, which skews the percentages. FIG. 3 shows a typical report generated by a prior art apparatus. As can be seen, the chips are classified according to their length (measured in mm) and their length (here, measured in inches). However, no provision is made for width and for the distribution of thickness of each chip, and it is impossible to ascertain from this report the digestibility index of the load of chips.

SUMMARY OF THE INVENTION

It is an object of the present invention to provide a wood chips analyser which provides more accurate results, and which is more flexible than in the prior art.

In accordance with the invention, this object is achieved with a wood chips analyser comprising:

- a transparent conveyor for conveying the chips from an upstream position to a downstream position, the transparent conveyor having a top and a bottom surfaces;
- means for feeding the chips to the transparent conveyor;
- means for spreading the chips on the transparent conveyor;
- a pair of cameras, one of the cameras facing the top surface of the transparent conveyor, the other camera facing the bottom surface of the transparent conveyor, both cameras being focused on an imaginary line crossing the transparent conveyor, each camera having an output;
- means for receiving the output of each camera and analysing the same in order to categorize the chips according to predetermined criteria and produce an output; and
- means for controlling the transparent conveyor, the pair of cameras, the means for feeding the chips, the means for spreading the chips and the means for receiving the output of each camera.

BRIEF DESCRIPTION OF THE DRAWINGS

The present invention and its advantages will be more easily understood after reading the following non-restrictive description of preferred embodiments thereof, made with reference to the following drawings in which:

FIG. 2 is a schematic representation of an evaluation report generated by the analyser of FIG. 1;

FIG. 3 is a schematic representation of an evaluation report generated by a prior art analyser.

DESCRIPTION OF A PREFERRED EMBODIMENT OF THE INVENTION

Figure 1:
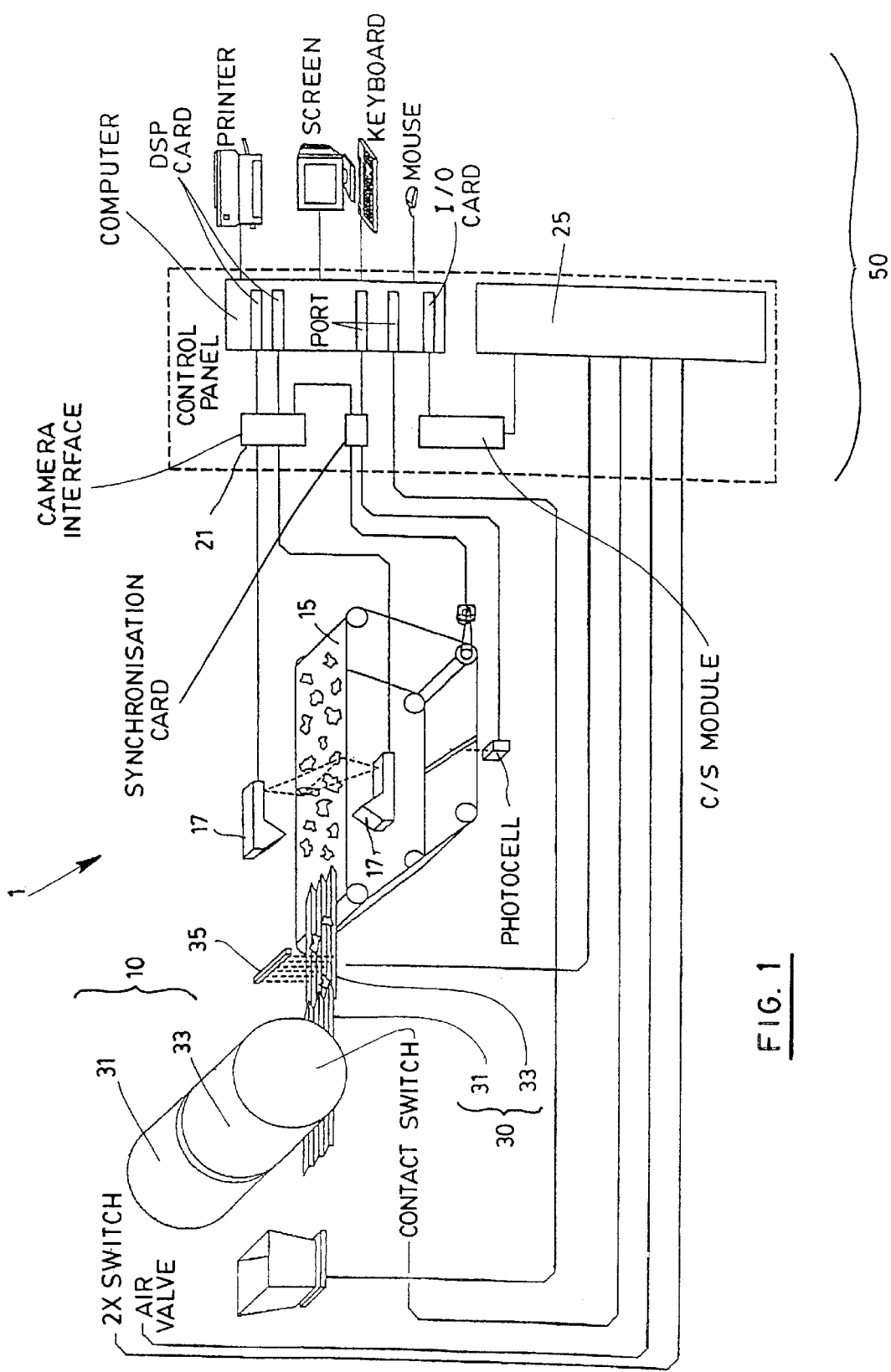
FIG. 1 is a schematic representation of a wood chips analyser according to a preferred embodiment of the invention.

Referring now to FIG. 1, the present invention concerns a wood chips analyser 1 for sorting and analysing a sample from a load of chips. As mentioned above, a sample of a load of chips is always analysed prior to feeding the load into a pulper. This step is to determine the characteristics of the load, and thus the proportions of the chemicals which must be added to make paper out of the pulp. The present invention concerns a machine for performing this analysis. In broad terms, the sample is weighed, the dust is extracted from the sample, and then each chip is measured and classified. A report is generated after each chip from the sample has been measured, and appropriate decisions are made based on the report.

The analyser 1 generally comprises a transparent conveyor 15 for conveying the chips from an upstream position to a downstream position, the transparent conveyor having a top and a bottom surfaces. A pair of cameras 17 are provided in the machine, one of the cameras facing the top surface of the transparent conveyor, the other camera facing the bottom surface of the transparent conveyor, both cameras being focused on an imaginary line crossing the transparent conveyor and each camera having an output. Means 10 are provided for feeding the chips to the transparent conveyor, as well as means 30 are for spreading the chips on the transparent conveyor. Means 50 is provided for receiving the output of each camera, for analysing the output of each camera in order to classify the chips, for controlling the transparent conveyor, the pair of cameras, the means for feeding the chips, and the means for spreading the chips. Preferably, the means 50 are embodied in a conventional personal computer system, properly programmed to control all of the elements of the analyser, i.e. to receive and store the weight of the sample-and the weight of the dust; to control the operation of the drums and the trays; to receive, store and process the density information provided by the photocell; to receive, store and process the outputs generated by each camera and output a representation of each chip in a three-dimensional matrix; to arrange the representation of each chip into a report according to predetermined and modifiable criteria; and to control the transparent conveyor.

In more detail, the means 10 for feeding the chips to the transparent conveyor preferably comprise a sifting drum 31, for sifting out any dust present in a sample, and a spreading drum 33, for performing a first spreading out of the chips, both of which rotate about their central axis. The dust that is sifted out is collected on a platter lying on a scale in order to measure the weight of the dust. In order to further spread the chip prior to having them conveyed on the transparent conveyor, the means 30 for spreading the chips include at least one, and more preferably two, vibrating trays 31, 33. These trays insure that chips are not stacked one on top of the other and insure that all of the chips are oriented horizontally, and in cooperation with a photocell 35, measure the density of the chips. This information is sent to the means 50 for controlling the machine 1.

The chips, after having been sifted and spread, are conveyed to the transparent conveyor 15. On each surface of the conveyor, cameras 17 are placed. Each camera has an output and is used to make a three-dimensional representation of each chip.

The output of the cameras is sent to the means 21, which is essentially an image acquisition system. The information provided by the cameras is used to measure each chip, and for each chip a form is extracted, represented by a three-dimensional matrix.

The representation in three dimensions of each chip allows the measurement of the chips with very high accuracy, and permits a treatment of the information according to easily modifiable criteria. A digestibility index is defined to reflect the thickness of each pixel of each chip. An additional advantage of using optical measurements (or more precisely digital image processing) is that the intensity of each pixel generated by each camera can also be measured. This can be used to generate an index of the presence of bark on each chip.

Figure 4:
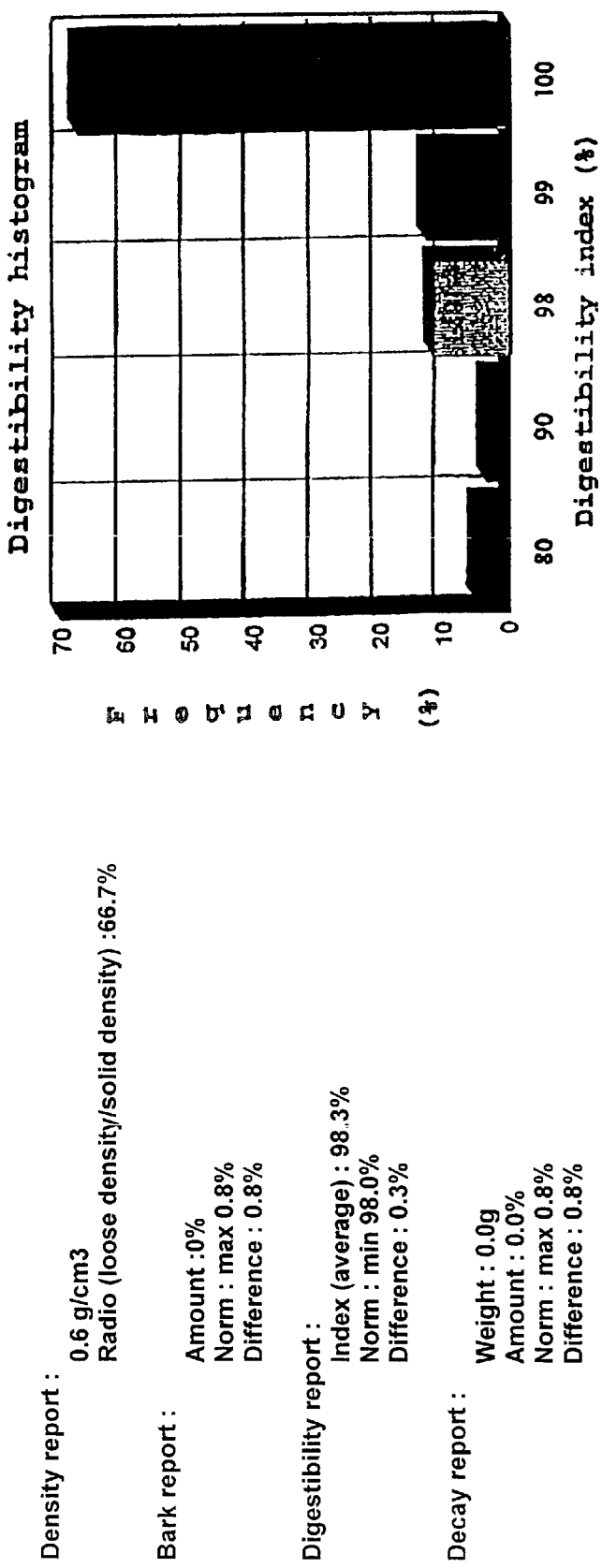
FIG. 4 is a histogram of the digestibility index.

The analyser 1 according to the present invention produces a report for individual samples, or for a group of samples. As an example of the type of report that can be generated, FIGS. 2, 3 and 4 represent typical reports that can be generated by the analyser 1 of the present invention. Particularly, FIG. 2 is an optical classification of the length and the thickness of each pixel of each chip as a percentage of the measured volume. This classification is extremely precise, since it is based on the three-dimensional form of each chip. It should be noted that the categories of lengths and thicknesses can be modified at will.

FIG. 3 represents a report generated by the analyser of the present invention, but where the report is tailored to emulate the reports generated by prior art mechanical analysers.

FIG. 4 is an histogram of the digestibility index of the sample of the chips. Essentially, the occurrence of a given index is graphed. The histogram of FIG. 4 shows that almost seventy percent of the chips in this particular sample are 100% digestible.

Although the present invention has been explained hereinabove by way of a preferred embodiment thereof, it should be pointed out that any modifications to this preferred embodiment within the scope of the appended claims is not deemed to alter or change the nature and scope of the present invention.

What is claimed is:

1. A wood chips analyser comprising:

a transparent conveyor for conveying the chips from an upstream position to a downstream position, the transparent conveyor having a top and a bottom surfaces;

means for feeding the chips to the transparent conveyor;

means for spreading the chips on the transparent conveyor;

a pair of cameras, one of the cameras facing the top surface of the transparent conveyor, the other camera facing the bottom surface of the transparent conveyor, both cameras being focused on an imaginary line crossing the transparent conveyor, each camera having an output;

means for receiving the output of each camera and analysing the same in order to categorize the chips according to predetermnined criteria and produce an output;

means for controlling the transparent conveyor, the pair of cameras, the means for feeding the chips, the means for spreading the chips and the means for receiving the output of each camera; and means for collecting and weighing dust contained in said chips, said means for collecting and weighing being placed upstream of said means for spreading the chips on the transparent conveyor.

2. A wood chips analyser according to claim 1, wherein:

said means for spreading the chips include at least one vibrating tray, and said analyser further includes a plurality of photocells located above the at least one tray for assessing the chips density, the photocells having an output operatively connected to the means for receiving the output of each camera.

3. A wood chips analyser according to claim 2, wherein said means for spreading the chips include two of said at least one vibrating tray, one of the vibrating trays slightly overlapping the other vibrating tray.

4. A wood chips analyser according to claim 2, wherein said means for feeding the chips includes at least one drum for receiving a load of chips and gradually feeding the chips to the at least one vibrating tray.

5. A wood chips analyser according to claim 4, wherein said means for feeding the chips includes two of said at least one drum, the first drum being a sieving drum and the second drum being a spreading drum.

* * * * *